US007250173B2

(12) United States Patent
Weinstock et al.

(10) Patent No.: US 7,250,173 B2
(45) Date of Patent: Jul. 31, 2007

(54) USE OF PARASITIC BIOLOGICAL AGENTS FOR PREVENTION AND CONTROL OF AUTOIMMUNE DISEASES

(75) Inventors: Joel V. Weinstock, Iowa City, IA (US); David E. Elliott, North Liberty, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 10/779,249

(22) Filed: Feb. 13, 2004

(65) Prior Publication Data

US 2004/0202671 A1    Oct. 14, 2004

Related U.S. Application Data

(62) Division of application No. 09/209,732, filed on Dec. 11, 1998, now Pat. No. 6,764,838.

(60) Provisional application No. 60/070,147, filed on Dec. 31, 1997.

(51) Int. Cl.
| | |
|---|---|
| *A61K 39/00* | (2006.01) |
| *A61K 39/38* | (2006.01) |
| *A61K 39/002* | (2006.01) |
| *A61K 39/005* | (2006.01) |
| *A61K 39/008* | (2006.01) |

(52) U.S. Cl. .............................. 424/265.1; 424/269.1; 424/184.1

(58) Field of Classification Search ............. 424/184.1, 424/265.1, 520, 269.1; 530/350, 412, 855
See application file for complete search history.

(56) References Cited

U.S. PATENT DOCUMENTS

| | | | |
|---|---|---|---|
| 4,396,600 A | 8/1983 | Messineo et al. .............. 424/88 |
| 6,765,838 B2* | 7/2004 | Matsumoto et al. ......... 365/222 |
| 2003/0039666 A1* | 2/2003 | Weinstock et al. ........ 424/234.1 |
| 2004/0202671 A1* | 10/2004 | Weinstock et al. ........ 424/184.1 |
| 2004/0253709 A1* | 12/2004 | Schramm et al. ......... 435/252.3 |
| 2005/0118655 A1* | 6/2005 | Weinstock et al. .......... 435/7.22 |
| 2006/0024333 A1* | 2/2006 | O'Connor ................. 424/265.1 |

FOREIGN PATENT DOCUMENTS

| | | |
|---|---|---|
| EP | 0 524 834 A2 | 1/1993 |
| WO | WO 93/23063 | 11/1993 |
| WO | WO 95/24425 | 9/1995 |
| WO | WO 96/29082 | 9/1996 |
| WO | WO 99/33479 A1 * | 7/1999 |
| WO | WO 00/25810 | 5/2000 |
| WO | WO 2006/014907 A2 * | 2/2006 |

OTHER PUBLICATIONS

Bellon et al, J. Clin. Lab. Immunol., 1982, 8:133-136.*
Dangolla et al, Preventive Vet. Medicine, 1996, 27:197-209.*
Ely et al, Lab. Animal Science, 1994, 44/3:211-216.*
Swindle, J. Investigative Surgery, 1996, 9:267-271.*
Petkevicius et al, Helminthologia, 1996, 33/4:173-180.*
Eriksen et al, Vet. Parasitology, 1992, 41:137-149.*
Wynn et al, J. Immunology, 1998, 160:4473-4480.*
Oswald et al, J. Immunology, 1994, 153:1707-1713.*
Pearce et al, J. Expt. Med., 1991, 173:159-166.*
Pearce et al, PNAS, USA, 1988, 85:5678-5682.*
Metwali et al, J. Immunology, 1996, 157:4546-4553.*
Kullberg et al, J. Immunology, 1992, 148/10:3264-3270.*
Bancroft et al, Eur. J. Immunol., 1994, 24:3113-3118.*
Bowman et al, Folia Parasitology, 1991, 38:245-253.*
Elliott, METHODS: A Companion to Methods in Enzymology, 1996, 9:255-267.*
Coker et al, Proceedings Soc. for Exp. Biol. and Med., 1956, 92:780-782.*
Elise et al, Parasitology, 1990, 100:479-489.*
Brown et al, Center for Tropical and Subtropical Aquaculture Publication No. 116: I-IV, pp. 1, 3-28, 1995.*
Thaumaturgo et al, Mem. Inst. Oswaldo Cruz, Rio de Janeiro, 2001, 96/Suppl.: 79-83.*
Sewell et al, International Immunology, 2003, 15/1:59-69.*
Elliott et al, Gastroenterology, 2002, 122/4 Suppl 1:A389 abstract only.*
Elliott et al, Am. J. Physiol. Gastroenterol. Liver Physiol., 2003, 284:G385-G391.*
Imai et al, Current Topics in Medicinal Chemistry, 2004, 4:539-552.*
Harnett et al, Current Topics in Medicinal Chemistry, 2004, 4:553-559.*
McInnes et al, J. Immunology, 2003, 171:2127-2133.*
Nagayama et al, J. Immunology, 2004, 173:2167-2173.*
Summers et al, Applied J. Gastroenterology, 2003, 98/9:2034-2035.*
Elliott et al, Current Opinion Gastroenterology, 2004, 21:51-56.*
Elliott, Gastroenterology Clinics of North America, 1996, 25/3:599-625.*
Summers et al, Gut, 2005, 54:87-90.*
Elliott et al, Digestive and Liver Disease, 2000, 32/Suppl. 1:A26 abstract only.*
Summers et al, Digestive and Liver Disease, 2000, 32/Suppl. 1:A26 abstract only.*

(Continued)

*Primary Examiner*—Nita M. Minnifield
(74) *Attorney, Agent, or Firm*—Edwards Angell Palmer & Dodge

(57) ABSTRACT

The invention relates to a method of treating an excessive immune response including an aberrant/enhanced Th1 response by administering a helminthic parasite preparation in an amount sufficient to reduce the excessive immune response in an individual. This invention is generally directed to autoimmune diseases which involve an excessive immune response or an aberrant/enhanced Th1 response. More specifically, the present invention is directed to the treatment of Crohn's disease and ulcerative colitis, both known as IBD. While the present invention discloses specific information about the treatment of IBD, the disclosure is in no way limiting. Additionally, rheumatoid arthritis, type 1 diabetes mellitus, lupus erythematosis, sarcoidosis and multiple sclerosis can be treated by the methods and compositions disclosed therein.

2 Claims, 3 Drawing Sheets

OTHER PUBLICATIONS

Summers et al, Gastroenterology, 2005, 128:825-832.*
Summers et al, Nature Clinical Practice Gastroenterology & Hepatology, 2005, 2/2:62-63.*
Metwali et al, Gastroenterology, Apr. 2006, 130/No. 4, Suppl. 2, p. A41 meeting abstract.*
Barriga, O.O., (1978), "Depression of cell-mediated immunity following inoculation of *Trichinella spiralis* extract in the mouse", *Immunology*, 34:167-173.
Dreyer, G. et al., (1996), "Patterns of Detection of *Strongyloides stercoralis* in Stool Specimens: Implications for Diagnosis and Clinical Trials", *Journal of Clinical Microbiology*, 34(10): 2569-2571.
PCT International Search Report of Application No. PCT/US98/26458, 1998.
Supplementary Partial European Search Report of Application No. EP 98 96 3124, 1998.

* cited by examiner

USE OF PARASITIC BIOLOGICAL AGENTS FOR PREVENTION AND CONTROL OF AUTOIMMUNE DISEASES

This application is a divisional which claims priority under 35 U.S.C. § 120 to U.S. patent application Ser. No. 09/209,732 filed Dec. 11, 1998, now U.S. Pat. No. 6,764,838 which claims benefit under 35 U.S.C. § 119(e) to U.S. Provisional Application Ser. No. 60/070,147 filed Dec. 31, 1997, the entirety of each is incorpdrated herein by reference.

FIELD OF THE INVENTION

This invention relates to the prevention and/or treatment of a condition or disease state in an individual which results from an excessive immune response.

BACKGROUND OF THE INVENTION

Parasites are living entities that dwell on or in other creatures during some part of their life cycles, drawing nourishment from the host. Parasites that inhabit the intestines have a complex interplay with the mucosal immune system. They must establish a tranquil relationship with host mucosal defenses to survive.

Helminths are elaborate multicellular worms with complex life cycles and development. The nematodes (non-segmented roundworms) and the platyhelminths (flatworms) are the two groups of helminths that colonize the human intestines. Perhaps more than a third of the population of the world currently shelter one or more of these organisms. The life-time exposure rate, however, is actually much more. The prevalence of helminths is highest in warm climates and in populations subject to crowding, poor sanitation and impure food supply. Inflammatory bowel disease (IBD), rheumatoid arthritis and autoimmune diseases are rare in these same regions.

Nematodes that frequently inhabit the human gut are *Ascaris lumbricoides, Enterobius vermicularis* (pin worm), *Trichuris trichiura* (whipworm), *Ancylostoma duodenale* and *Necator americanus* (hookworms), and *Strongyloides stercoralis*. *Trichinella spiralis* infests the small intestine briefly.

The platyhelminths include the trematodes and cestodes. The most common adult trematodes that reside in the human intestines are *Fasciolopsis, Echinostoma* and *Heterophyes* species. Those that live in the biliary system include *Clonorchis sinensis, Opisthorchis viverrini* and *felineus*, and *Fasciola hepatica*. *Schistosoma* dwell in the venous system, but several species chronically affect the gut by the passage of eggs through the intestinal wall. Adult cestodes commonly infecting humans are *Diphyllobothrium* species (fish tapeworm), *Taenia saginata* (beef tapeworm), *Taenia solium* (pork tapeworm) and *Hymenolepsis nana* (dwarf tapeworm).

The host acquires various helminthic species through contact with soil, food or water contaminated with the infective form of the parasite. Children most frequently harbor helminthic infections because of their close contact with soil and suboptimal hygienic practices. Helminths incite an intestinal Th2 response, which can cause worm expulsion or limit the magnitude of infection. Most children living in non-industrialized countries have these parasites. Many helminthic species survive for years within the gut, biliary tree or mesenteric veins making thousands of eggs daily. Thus, beginning in childhood, these worms and/or their ova release molecules that bathe the intestinal mucosal surface for years inciting Th2-type inflammation. Dysregulation of the immune system leading to an excessive Th1 response may be the cause of several human diseases. Some diseases due to dominant Th1 responses include IBD, rheumatoid arthritis, sarcoidosis, multiple sclerosis, and insulin-dependent diabetes melitis.

IBD is more common in temperate climates. It is not known what causes the geographic differences. Observations suggest an environmental exposure unique to temperate countries and highly industrialized societies predisposes to the development of IBD. An alternative explanation is that it is unhealthy to be raised in an "over clean" environment. It is proposed herein that the major environmental factor predisposing to IBD is underexposure during childhood to intestinal helminths, which promote strong Th2-type inflammation.

The frequency of CD has increased substantially over the last 40 years. It is most prevalent in temperate regions that are highly industrialized. This suggests that there is some critical environmental factor responsible for the change in frequency. Also, ulcerative colitis is rare in underdeveloped countries. It is proposed according to the invention that the absence of exposure to intestinal helminthic infections in childhood is an important environmental factor favoring the development of CD and perhaps ulcerative colitis (UC).

People in industrialized countries are living in increasingly hygienic environments and are acquiring helminths much less frequently. The decreasing frequency of helminthic infections appears to correlated with the increasing prevalence of CD. A case in point is the marked increase in the frequency of CD in young Asians and Africans after residing in Israel for greater than 10 years. Also, the frequency of helminthic infestation differs between the Jewish Israelis and Arabs. In 1969, stool examinations of hospitalized patients in Arab-predominant East Jerusalem contained helminthic ova over 60% of the time. The frequency in Israeli-predominant East Jerusalem was 10% or less.

Thus, It is possible that the failure to acquire helminths and to experience mucosal Th2 conditioning predisposes to CD and UC. There is a need to combat CD and UC by re-colonization of the gastrointestinal tract with these organisms which may afford protection.

One object of the invention is to prevent or treat an excessive immune response in an individual. The excessive or aberrant immune response can be caused by an autoimmune disease, for example, IBD, rheumatoid arthritis, type 1 diabetes melitis, lupus erythematosis, sarcoidosis and multiple sclerosis.

Further, it is an object of the instant invention to provide a method of vaccinating an individual against autoimmune disease, for example, IBD, rheumatoid arthritis, type 1 diabetes melitis, lupus erythematosis, sarcoidosis and multiple sclerosis.

It is an object of the present invention to provide a method of creating an immune environment in an individual that is conducive to ameliorating IBD.

It is an object of the present invention to provide a pharmaceutical composition comprising a helminthic parasite and a pharmaceutically acceptable carrier.

It is a further object of the present invention to provide a pathogen-free helminthic parasite and an acceptable pharmaceutical carrier.

It is another object of the present invention to provide a method of preparing pathogen-free helminthic parasites.

SUMMARY OF THE INVENTION

The instant invention presents a method of preventing or treating an excessive immune response in an individual by administering an effective amount of an helminthic parasite preparation to reduce the excessive immune response in the individual.

The invention encompasses a method of treating an excessive immune response, including an aberrant/enhanced Th1 response, comprising administering a helminthic parasite preparation in an amount sufficient to reduce the excessive immune response.

As used herein, the term "helminth parasite preparation" refers to any one of a whole parasite, a parasite extract, parasite eggs, parasite egg extract, parasite larvae, parasite larvae extract, parasite cercariae and parasite cercariae extract.

The helminthic preparation may be selected from the group consisting of helminiths that naturally colonize humans and helminths that colonize animals but may protect humans from an excessive Th1 response.

In other preferred embodiments of the invention, the helminth parasite is a nematode, and may be selected from the group such as *Ascaris lumbricoides, Enterobius vermicularis, Trichuris trichiura, Ancylostoma duodenale* and *Necator americanus, Strongyloides stercoralis* and *Trichinella spiralis.*

In other preferred embodiments of the invention, the helminthic parasite is a platyhelminth, and may be selected from the group consisting of trematodes and cestodes, such as *Fasciolopsis, Echinostoma* and *Heterophyes* species, *Clonorchis sinensis, Opisthorchis viverrini, Opisthorchis felineus, Fasciola hepatica, Schistosoma* species, *Diphyllobothrium* species, *Taenia saginata, Taenia solium* and *Hymenolepsis nana.*

In other preferred embodiments, the helminthic parasite is selected from the group consisting of filarial parasites and lung flukes.

In additional embodiments, the helminthic parasites are selected from the group consisting of *Trichuris muris, Trichinella spiralis, Nippostrongylus prasiliensis, Heligmonsomoides polygyrus, Hymenolepsis nanan, Angiostrongylus* species, *Trichuris suis, Ascaris suum, Trichuris vulpis, Toxocara* species, *Gnathostoma* species, *Ancylostoma* species, *Anisakis* species and *Pseudoterranova* species.

The invention also encompasses a method of preventing or treating an autoimmune disease in an individual comprising administering a helminthic parasite in an amount sufficient to prevent or treat the autoimmune disease in an individual.

As used herein, the term "autoimmune disease" refers to diseases such as IBD, rheumatoid arthritis, type 1 diabetes mellitus, lupus erythematosus, sarcoidosis and multiple sclerosis The "effective dosage" amount of the helminthic parasite preparation is dependent upon the specific cause for the excessive or aberrant immune response, and is addressed in detail below.

As used herein, the term "excessive" or "aberrant" immune response refers to a T helper cell type 1 (Th1) response in which the activity of T helper 1 cells is elevated in an individual relative to the activity of such cells in an individual who is not affected by the disease. Typically, the elevation of the Th1 response in the diseased individual will be at least 2-fold, and possible 5-fold-10-fold above the Th1 response in an individual who is not diseased. Th1-type inflammations produce large amounts of IFN-γ and TNFα, which in turn stimulate a strong cellular immune reaction. These are some of the cytokines that may be measured to indicate an excessive or aberrant Th1 response, as described in detail hereinbelow.

Preferably, the helminthic parasite is selected from the group consisting of parasite, parasite extract, parasite eggs, parasite egg extract, parasite larvae, parasite larvae extract, cercariae and cercariae extract.

The invention also encompasses a method of treating IBD comprising administering a helminthic parasite preparation in an amount sufficient to reduce IBD.

The invention also encompasses a method of vaccinating an individual against a disease involving an excessive immune response comprising administering a helminthic parasite preparation in an amount sufficient to prevent the excessive immune response.

The invention also encompasses a pharmaceutical composition comprising a helminthic parasite preparation, and a pharmaceutically acceptable carrier.

Further features and advantages of the invention will become more fully apparent in the following description of the embodiments and drawings thereof, and from the claims.

DETAILED DESCRIPTION OF THE INVENTION

Figure 1A:
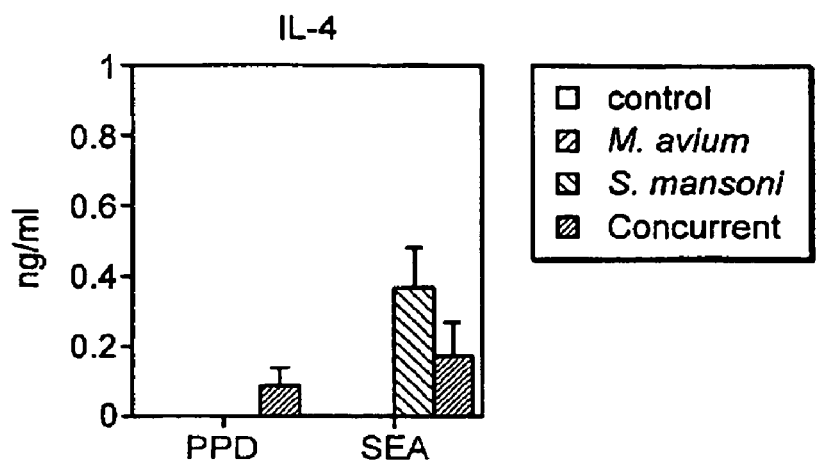
FIG. 1. The figure describes the concentrations of IFNγ, IL-4 and IL-5 measured in spleen cell supernatants of mice infected with *M. avium, S. mansoni* or both organisms. Splenocytes ($4 \times 10^5$/well) were cultured in vitro for 48 h at 37° C. in 200 μl of medium in the presence or absence of optimal concentrations of PPD or SEA. Cytokine secretion was quantified by ELISA.

The present invention is based upon the recognition that diseases that involve excessive or aberrant Th1 immune responses are treatable by administration of a helminthic parasite preparation.

The invention relates to a method of treating an excessive immune response including an aberrant/enhanced Th1 response by administering a helminthic parasite preparation in an amount sufficient to reduce the excessive immune response in an individual. This invention is generally directed to autoimmune diseases which involve an excessive immune response or an aberrant/enhanced Th1 response. More specifically, the present invention is directed to the treatment of Crohn's disease and ulcerative colitis, both known as IBD. While the present invention discloses specific information about the treatment of IBD, the disclosure is in no way limiting. Additionally, rheumatoid arthritis, type 1 diabetes mellitus, lupus erythematosis, sarcoidosis and multiple sclerosis can be treated by the methods and compositions disclosed therein.

The entire disclosure of each of the literature references cited hereinafter are incorporated by reference herein.

Helminthic Parasites Useful According to the Invention

In defining a helminthic parasite, there are two groups. The first group is helminthic parasites that naturally colonize humans and the second group is helminthic parasites that colonize animals, but may afford protection to humans.

In the first group, helminthic parasites are elaborate multicellular worms with complex life cycles and development. The nematodes (non-segmented round worms), and the platyhelminths (flat worms) are two groups of helminths that colonize the human intestines. In accordance with the present invention, any one of a number of helminth parasites that naturally colonize humans or animals will provide the intended results.

Nematodes that frequently inhabit the human gut are *Ascaris lumbricoides, Enterobius vermicularis* (pin worm), *Trichuris trichiura* (whipworm), *Ancylostoma duodenale* and *Necator americanus* (hookworms), and *Strongyloides stercoralis. Trichinella spiralis* infests the small intestine briefly.

The platyhelminths include the trematodes and cestodes. The most common adult trematodes that reside in the human intestines are *Fasciolopsis, Echinostoma* and *Heterophyes* species. Those that live in the biliary system include *Clonorchis sinensis, Opisthorchis viverrini* and *felineus*, and *Fasciola hepatica. Schistosoma* dwell in the venous system, but several species chronically affect the gut by the passage of eggs through the intestinal wall. Adult cestodes commonly infecting humans are *Diphyllobothrium* species (fish tapeworm), *Taenia saginata* (beef tapeworm), *Taenia solium* (pork tapeworm) and *Hymenolepsis nana* (dwarf tapeworm).

Other helminths of interest include the filarial parasites and the lung flukes. These do not have a gut phase, but stimulate strong Th2-type responses.

The second general group of helminthic parasites that can be utilized in the present invention include helminths that colonize animals, but may afford humans protection against Th1-mediated diseases. These include *Trichuris Muris* (mouse whipworm), *Trichinella spiralis, Nippostrongylus brasiliensis, Heligmonsomoides polygyrus* and *Hymenolepsis nana*, all of which are intestinal helminths that infect mice. Additionally, *Angiostrongylus* is a rat helminth. *Trichuris suis* and *Ascaris suum* are pig helminths that can infect humans. *Trichuris vulpis, Toxocara* species, *Gnathostoma*, and *Ancylostoma* are dog or cat helminths that also can infect humans. *Anisakis* and *Pseudoterranova* are nematodes of marine mammals that can transmit to humans. Bird schistosomes can transiently infect humans. Such schistosomes include *S. douthitti, Trichobilharzia ocellata, T. stagnicolae, T. physellae,* and *Gigantobilharzia huronensis*.

Diseases Treatable According to the Invention

A. Inflammatory Bowel Diseases (CD and UC):

Epidemiological data suggest a genetic susceptibility to the development of Crohn's disease (CD) and ulcerative colitis (UC). The incidence of CD in industrialized societies has increased from the 1950s until the mid 1980s, and now is from 1 to 8 per 100,000 persons per year. This suggests that unknown changes in our environment have effected the frequency of CD.

While the cause of IBD remains undetermined, it is presumed to result from dysregulation of the intestinal mucosal immune system. Inflammatory cells in the mucosa normally protect us from luminal contents. This highly effective chronic inflammation is tightly controlled to limit tissue injury. IBD may result from inappropriately vigorous immune responses to luminal factors. CD appears to be an overly vigorous Th1-type inflammation that produces IFN-$\gamma$ and TNF$\alpha$. The nature of UC is less well defined.

There are several animal models of chronic intestinal inflammation, for example, as reported by Elliott et al. (Elliott et al., 1998, *Inflammatory Bowel Disease and Celiac Disease*. In: *The Autoimmune Diseases*, Third ed., N. R. Rose and I. R. MacKay, eds. Academic Press, San Diego, Calif.). An important advance is the recent discovery that some mice with genetically engineered gene deletions can develop chronic bowel inflammation similar to IBD, see Elson et al., 1995, *Gastroenterology* 109:1344. These include mutant mice bearing targeted deletions for IL-2, IL-10, MHC class II or TCR genes among others. Using some of the models, Berg et al., 1996, *J. of Clin. Investigation* 98: 1010, Ludviksson et al., 1997, *J. of Immunol*. 158:104, and Mombaerts et al., 1993, *Cell* 75:274 have shown that a dysregulated immune system itself can mediate intestinal injury. The mucosal inflammation of several of these models generates large amounts of IFN-$\gamma$ and TNF-$\alpha$ suggesting that excess production of Th1-type cytokines is one common mechanism underlying the pathogenesis of disease. Also, blocking Th1 circuitry prevents the inflammation. CD is a Th1 response. Thus, these models may have direct implications regarding the immunopathology of this human disease process.

B. Rheumatoid Arthritis (RA):

RA is a chronic disease featuring persistent inflammatory synovitis, usually involving peripheral joints in a symmetric distribution. This inflammation can lead to bone erosions, cartilage damage and joint destruction. It is an affliction of about 1% of the population. The prevalence increases with age, and women are affected more frequently than men. The propagation of RA is an immunologically mediated event driven by CD4+ Th1 cells.

C. Insulin-dependent, Juvenile Diabetes Meritus (DM) (type 1):

Type 1 DM is a disease that usually begins during early adulthood and that results from the inability to produce insulin in response to increasing blood sugar. This persistent high blood sugar and inability to properly metabolize glucose causes metabolic disturbances that eventually damage the eyes, kidneys, heart and other organs. Taking insulin parenterally can partially control these metabolic problems. Type 1 DM results from an autoimmune attack on the pancreatic beta cells, which are the source of insulin. Activated macrophages and cytotoxic T cells surround and destroy the pancreatic beta cells. Genetic susceptibility and poorly defined environmental events trigger the disease process.

D. Lupus Erythematosus (LE):

LE is a systemic autoimmune disease that is most frequent in women of early to middle adulthood. The tissue damage is caused by autoantibodies and hyper-reactive regulatory T cells. The abnormal immune response allows sustained production of pathogenic autoantibodies and immune complexes. This leads to damage of the musculoskeletal, cutaneous, hematologic, renal and other systems. The abnormal immune response probably depends upon the interaction of multiple hereditary and environmental factors.

E. Sarcoidosis:

Sarcoidosis is a chronic granulomatous disease of the lungs and other organs of unknown cause. Most patients present between the ages of 20-40. The most frequent symptom is shortness of breath. The disease results from an exaggerated Th1-type, cellular immune response, probably to a limited number of antigens. Sarcoidosis develops throughout the world, and afflicts all races. However, there is remarkable diversity of the prevalence of sarcoidosis among certain ethnic and racial groups. For instance, the disease is rare in Poland, Southeast Asia and India.

F. Multiple Sclerosis (MS):

MS is a chronic relapsing, multifocal inflammatory disorder of the central nervous system that leads to focal demyelination and scarring of the brain. It is a frequent disease affecting about 350,000 Americans and which begins during early to middle adulthood. MS is an autoimmune disease mediated at least in part by Th1 cells. The lesions of MS resemble those induced by delayed hypersensitivity responses that contain activated T cells and macrophages. It is a disease of temperate climates, increasing in prevalence with distance from the equator.

Helminthic Parasite Preparations According to the Invention

A. Viable Organism Vaccines:

Viable helminthic parasite organisms may provide the most profound Th2 mucosal conditioning because of their relative longevity as compared to component vaccines. Viable organisms can be administered in either egg, larval, cercarial, or encysted larval forms depending on the helminth. Helminths that can colonize humans and a preparatory animal may be utilized.

The preparatory animal may need manipulation to allow high patency by the helminthic. Such manipulation can include treatment with agents that are immunosuppressive like glucocorticoids or azathioprine; agents that impede Th2 effects like anti-histamines, anti-cytokines, or recombinant cytokines; and agents that influence intestinal motility like anti-cholinergics or opiates. The animal's diet will be altered to reduce coarse fiber content. The animal may be a rat, pig, hamster, bird or other preparatory animal.

Preparatory animals are raised in specific pathogen-free (SPF) environments according to methods known in the art. They are tested to ensure absence of human bacterial, mycobacterial, and viral pathogens.

Eggs: Some intestinal helminths are acquired by ingestion of viable eggs. Helminths are maintained in SPF preparatory animals, for example, SPF pigs. To harvest eggs, the animals are given a special diet low in coarse fiber. Animals are given an oral purgative to induce defecation. Stool is collected and enzymatically digested to free eggs. Eggs are isolated from liquefied stool by flotation on density gradients, screen filtration, Visser filtration, or centrifugal elutriation. Preservation of eggs varies with the helminth used. Eggs from helminths that are resistant to dessication are dried, compounded with inert material, incorporated into an enteric capsule, and refrigerated. Eggs from helminths that are susceptible to dessication are preserved by refrigeration in liquid medium or by adding cryoprotectant and freezing in liquid nitrogen. Viable eggs are washed, mixed with chilled lactose-free pudding or other vehicle at the location for delivery. Eggs stored in glycerol-based cryoprotectant may not require washing. Eggs from each lot are tested for hatching rate to determine effective dosing. Eggs from each lot are tested for absence of bacterial and viral pathogens.

Larvae: Some helminths (i.e. hookworms) require a soil maturation phase before they can colonize humans. Eggs from these agents will be incubated under optimal conditions to mature the embryo, or hatch the egg and provide larval forms. Patients can be inoculated by subcutaneous injection of viable larvae.

Cercariae: Some helminths have complex life cycles that utilize an intermediate host. The intermediate host sheds the form able to colonize humans. Cercariae are the form for trematode helminths (i.e. flukes) shed by intermediate hosts like snails. Cercariae are isolated from colonized snails grown in SPF conditions. Cercariae are washed. These may be preserved by adding cryoprotectant and freezing in liquid nitrogen. Thawed or fresh cercariae are washed and injected subcutaneously to inoculate patients. Samples from each lot are tested for absence of pathogens and to determine effective dose.

Encysted Larvae: Some helminths (e.g. tapeworms) form encysted larvae or cysticerci in intermediate hosts. It is the encysted larval form that initiates human colonization. Encysted larva are removed from intermediate hosts, for example, cattle or fish or plants grown in SPF conditions. Cysts are washed free of remaining host tissue. Cysts may be preserved by adding cryoprotectant and freezing in liquid nitrogen. Cysts are thawed or used fresh, washed, mixed with chilled lactose-free pudding or other vehicle at the location for delivery and fed to individuals. Samples from each lot are tested for absence of pathogens and to determine effective dose.

B. Non-viable Component Vaccines:

Non-viable components of helminthic parasites provide sufficient Th2 conditioning of the immune response to prevent Th1-mediated pathology. Non-viable components are derived from eggs, larvae or adult worms.

Non-viable, intact schistosome eggs produce a strong Th2 response. Eggs are isolated from livers of preparatory animals (i.e. hamsters) grown under SPF conditions. Eggs are isolated by a method modified from that originally described by Coker and Lichtenberg, 1956, *Proceedings of the Soc. For Exp. Biol. & Med.* 92:780. The modifications consist of using phosphate buffered saline with glucose instead of 1.7% saline for incubation and washing steps along with decreasing the autolytic digestion time. These changes promote isolation of viable eggs. The method is as follows.

Infect golden hamsters with 1000 to 1500 cercariae. Allow the infection to mature (6 to 7 weeks). Remove the livers from the animals and place in 600 mOsm sterile phosphate buffered saline containing 5% glucose, 100 U/ml penicillin and 100 µg/ml streptomycin. The livers are allowed to autodigest for 24 hours at room temperature. Pulse homogenize the livers at low speed for 3 minutes in a cold Waring blender. Incubate the homogenate with collagenase (2 mg/ml) and trypsin (2 mg/ml) at 32° C. for one hour. Filter the homogenate through 50 and 80-100 mesh sieves to remove clumps of tissue and debris. Recover the eggs from the filtrate by passing over a 325 mesh sieve. The eggs will not pass through the screen. Flush the eggs off of the screen and into a 50 ml polypropylene centrifuge tube. Wash the eggs by repeated low speed (400×g) centrifugation in sterile phosphate buffered saline with 5% glucose. The eggs must be free of any collagenous debris. Count an aliquot of eggs in a 1 ml Sedwick chamber to determine total egg number.

Isolated eggs are suspended in saline and flash frozen in liquid nitrogen without cryoprotectant. This kills the egg.

Thawed eggs are injected subcutaneously, intramuscularly or intravenously, or at sites of Th1 inflammation to elicit strong Th2 responses. Eggs from other helminths may also be utilized.

Component vaccines may also be used that employ proteins, lipids, or carbohydrates isolated from parasite eggs. An example is schistosome soluble egg antigens (SEA). The method for preparing schistosome egg antigen has been previously described by Boros and Warren, 1970, *J. of Experimental Med*. 132:488 and is briefly given below.

Washed eggs are resuspended at 50,000 eggs/ml of phosphate buffered saline. This is transferred to a glass tissue homogenizer. The eggs are homogenized on ice. To insure that all shells are broken and miracidia are disrupted, an aliquot (5 µl) is removed for microscopic inspection. Transfer the homogenate to ultracentrifuge tubes. Centrifuge at 100,000×g for 2 hours at 4° C. Recover the aqueous fraction (SEA) and determine the protein content. Store the SEA in small aliquots at −70° C. This method may require modification to isolate the parasite egg products that most strongly promote Th2 conditioning, i.e., to achieve an optimal effective concentration, (100 µg SEA or 10,000 ova/animal). Eggs or soluble egg components are used to initiate Th2 responses or to boost Th2 responses previously initiated by colonization with viable helminths. Eggs or egg components are tested to confirm the absence of pathogens and endotoxin.

Component vaccines can also be developed from larvae and adult worms of helminthic parasites. Larvae or worms are isolated from preparatory animals grown in SPF conditions. Vaccines that employ non-viable intact organisms or proteins, lipids, or carbohydrates isolated from the helminth are prepared and utilized in a manner similar to that previously described for helminth eggs.

C. Maintenance of Helminth Organisms:

Helminths are cycled through intermediate and preparatory animals grown in SPF conditions. Samples of helminth populations are tested to ensure phenotypic stability such as colonization rates, fecundity, and susceptibility to antihelminthics.

Dosage, Administration and Pharmaceutical Formulations

Depending upon the helminthic parasites selected, treatment is delivered by one of several approaches. Individuals in need of treatment receive the infected form of the parasite (egg, cercariae or larvae) orally or parenterally depending upon the natural life cycle of the parasite selected. Alternatively, soluble worm or egg extracts can be given orally or parenterally to induce TH2 responses.

With regard to intestinal and liver helminths and schistosomes, they begin producing ova that appear in the stool about 30-60 days after inoculation. Quantifying the eggs in the stool proves satisfactory for assessing adequacy and intensity of infection. Aliquots of stool are processed by sucrose floatation to determine the total number of eggs in each specimen. Flotation over sucrose solution is a method frequently used to isolate eggs from stool for accurate counting as reported by Koontz and Weinstock, 1996, *Gastroenterology Clinics of N. America*, 25:435.

The helminthic parasite compounds of the invention may be formulated for administration in any convenient way, and the invention therefore includes within its scope pharmaceutical compositions comprising the helminthic parasite compound in accordance with the invention adapted for use in humans. Such compositions may be presented for use in conventional manner with the aid of any necessary pharmaceutical carriers or excipients.

The helminthic parasite compound according to the invention may be formulated for injection, and therefore, vaccine use, and may be presented in unit dose form in ampules, or multidose containers, if necessary, with an added preservative. The compositions may also take such forms as suspensions, solutions or emulsions of oily or aqueous vehicles and may contain formulatory agents such as suspending, stabilizing, and/or dispersing agents. Alternatively, the helminthic parasite may be in powder form or reconstituted with a suitable vehicle, e.g. sterile-pyrogen-free water, before use.

If desired, such powder formulation may contain an appropriate non-toxic base in order to ensure that the powder is reconstituted with water, the pH of the resulting aqueous formulation being physiologically acceptable.

The helminthic parasite compounds may also be formulated as suppositories, e.g. containing conventional suppository bases such as cocoa butter or other glycerides.

The helminthic parasite compounds may also be formulated to oral dosage with conventional fillers, carriers, and excipients. The amount of parasite administered to the individual in need thereof is an amount sufficient to prevent or treat the autoimmune disease. This amount may vary depending upon the disease being treated or prevented and the helminthic parasite, whether it is being administered intact, or as an egg, larvae, extract or cercariae.

Typically, when the parasites are administered for all autoimmune diseases discussed herein, the amount ranges from about 50 to about 50,000. More particularly, this amount may range from about 500 to about 5,000. When eggs are utilized, about 500 to about 5000 may be utilized to treat the autoimmune diseases disclosed herein. When extracts are administered, about 100 µg to about 10,000 µg are utilized to treat the autoimmune diseases. When larvae and cercariae are administered, the dosages may range from about 500 to about 5,000 in each case.

For prevention or vaccine use, the amounts of the parasites may be 500-5,000.

D. Determination of Th1 and Th2 Responses

In order to show the efficacy of the present invention, the Th1 and Th2 response must be distinguished. Metawali et al., 1996, *J. of Immunol*. 157:4546 has shown that in mice, it is possible to distinguish a Th1 from a Th2 response by histologic analysis, and by analysis of cytokine and immunoglobulin profiles. Further, Sandor et al., 1990, *J. of Exp. Med*. 171:2171 has shown that cell surface expression of Fcγ3 and MHC Class II molecules afford discrimination. In this procedure, small bowel and colon are examined histologically to determine the degree of mucosal inflammation, eosinophilia and mastocytosis. The latter cell types are indicative of a Th2 response. Mesenteric lymph nodes (MLN) and spleens can be dissociated into single cell suspensions for in vitro culture in microwell plates. Cells (1-2×10$^7$/well) in complete RPMI medium are cultured for up to 72 h in the presence or absence of worm antigen or anti-CD3 and then the supernatants are assayed for cytokines and immunoglobulins. IFN-γ, TNFα and IgG2a characterize a Th1 response, whereas IL-4, IL-5, IgE and IgG1 typify a Th2 reaction. Also, serum can be assayed for cytokine and immunoglobulin concentrations. Furthermore, dispersed inflammatory leukocytes are examined by flow cytometry for Fcγ3 expression on macrophages (Th1) and MHC Class II expression on B cells (Th2). Controls include serum, MLN and spleens from appropriate age-matched, littermate mice that hosted no parasite. Also, there are other markers of the Th1 vs Th2 responses.

A similar analysis can differentiate a human Th1 from a Th2 response. One examines inflamed tissue, isolated leukocytes from regions of inflammation and peripheral blood cells. Leukocytes are cultured in vitro alone or in the presence of parasite antigen or mitogens to stimulate cytokine release. IgG2 substitutes for IgG2a.

Cytokine Detection by Flow Cytometry: Splenocytes, MLN or intestinal inflammatory cells in RPMI complete medium are placed into 24-well tissue culture plates at $2 \times 10^6$ cells/well. Cells are incubated 4-6 h in the presence or absence of anti-CD3 or appropriate antigen with brefeldin A at 10 μg/ml. Brefeldin prevents exocytosis of proteins and promotes accumulation of the cytokine within the cell. For cytoplasmic cytokine detection, the cells are fixed in 2% paraformaldehyde at room temperature for 5 min following surface staining to distinguish cell subtypes. Cells are washed and re-suspended in 50 μl PBS 0.2% Saponin and 1 μg anti-cytokine antibody and incubated at room temperature for 20 minutes. Next, the cells are washed twice in Saponin and re-suspended in PBS/FCS. The specificity of the cytokine antibody staining is confirmed by pre-blocking the cells with an excess of un-conjugated antibody of the same isotype and cytokine specificity or by incubating the cells in the presence of recombinant cytokine. Phycoerythrin (PE)-labeled irrelevant antibody controls also are included to assess background staining. The cells are analyzed using flow cytometry.

ELISAs: ELISAs measure cytokine and antibody concentrations in cell supernatants from cells cultured in microtiter plates and manipulated as describe above. Many of these assays are already operational within our laboratory. Cytokines are assayed using two monoclonal antibodies (mAbs) in a two-site sandwich ELISA. The anti-cytokine mAbs are purified by ammonium precipitation from supernatants of antibody secreting hybridoma clones. Microtiter plates are coated with 50 μl of 1 ug/ml coating antibody in PBS containing Tween 20 (PBS-T), and incubated at 4° C. overnight. Then, wells are blocked by the addition of 150 μl of 10% FCS in PBS with incubation at 37° C. for 30 min. Standards comprise recombinant cytokine or cytokine-containing supernatants from Con A-activated spleen cells from schistosomiasis-infected mice. Sample and standard dilutions are made in RPMI containing 10% FCS (complete RPMI) in a separate 96-well flat bottom microtiter plate, and 50 μl volumes are transferred to the ELISA plates that have been washed three times in PBS-T. Samples are incubated in the assay plates for 1 h at 37° C. Appropriate mAb is conjugated to biotin. After washing three times in PBS-T, each well will receive 50 μl of antibody-biotin conjugate at 0.5 μg/ml in 1% BSA/PBS-T. Plates are incubated at room temperature for 1 h followed by washing three times in PBS-T. Streptavidin-horseradish peroxidase conjugate (75 μl) is added at 1 μg/ml in 1% BSA/PBS-T and incubated at room temperature for 1 h. Plates are washed 10 times in fresh PBS-T, and 100 μl of substrate (2,2'-azino(3-ethylbenzthiazoline sulfonic acid) at 1 mg/ml in 44 mM $Na_2HPO_4$, 28 mM citric acid, and 0.003% $H_2O_2$ is added. The colored product is measured at a wavelength of 405 nm with a reference wavelength of 490 nm, using a multiscan microplate reader.

Immunoglobulins are quantified using anti-isotype specific ELISAs. Affinity-purified goat anti-IgM, -IgG1, -IgG2a, -IgG2b, -IgG3, -IgA and -IgE are used as capture antibodies and absorbed to flexible polyvinyl microtiter dishes at 10 μg/ml. After addition of culture supernatants, incubation and washing, appropriate isotype alkaline-phosphatase-conjugated goat anti-Immunoglobulin is used to detect total mouse Immunoglobulin bound to the plates. Standard curves are generated using purified Immunoglobulin. To measure parasite antigen-specific antibody, soluble antigen is biotinylated and used to detect bound mouse Immunoglobulin. The plates are analyzed on a ELISA reader at 410 nm, and concentrations of total Immunoglobulin are determined using the standard curve and best-fit analysis software. Antigen-specific antibody concentrations are compared relative to the O.D. readings, since soluble parasite antigen is not a defined antigen that permits precise quantitation.

ELISPOT Assays: ELISPOT assays are established to count lymphocytes secreting either polyclonal antibody or cytokines. Ninety-six-well nitrocellulose-backed microtiter plates are coated overnight at 4° C. with 1 μg/ml of either anti-Immunoglobulin or anti-cytokine antibodies in PBS-T. The plates then are blocked with PBS containing 10% FCS and washed extensively with PBS-T.

Serial dilutions of a single cell suspension, starting with $5 \times 10^4$ cells/well, are incubated on the plate for 5 h at 37° C. in a humidified 5% $CO_2$ atmosphere. The plates are washed with PBS-T and overlaid with biotinylated anti-Immunoglobulin or -cytokine antibodies overnight at 4° C. Next, plates are washed and treated with streptavidin-glucose oxidase-conjugate for 2 h and washed again.

The antibody or cytokine secreted by single cells is visualized with substrate. The colorimetric reaction is halted after 30 min by washing and spots enumerated under 30× magnification. The dilution of cells producing 10-50 spots/well is used to calculate the total number of secreting cells per sample. Controls include wells coated with inappropriate goat antibody or inappropriate antigen, or left uncoated.

A modification of the assay using soluble antigen to coat the wells permits quantitation of parasite antigen-specific, Immunoglobulin secreting B cells also. Briefly, for example, plates are coated with adult *T. Muris* antigen at 0.25 μg/well or appropriate irrelevant control antigen. Cells are added to the wells after washing. After appropriate incubation, the plates are washed again and treated as described above.

Statistical Methods: Some data are analyzed by the one sample t-test to determine whether mean values significantly differ from zero. Paired t-test is used to analyze differences between group means. Analysis of variance and Dunnett's t-test is used to analyze multiple comparison data.

Evidence of the presence of an autoimmune disease and its cure or amelioration is needed to determine the need for treatment and to monitor treatment progress. The following procedures are utilized to measure the clinical parameters of the noted diseases.

1. Inflammatory Bowel Disease

Evaluation of Inflammation: In mice, clinical evidence of disease includes weight loss, diarrhea, rectal prolapse and histological evidence of intestinal inflammation. Thus, improvement in these parameters would signify amelioration of disease.

To grade intestinal inflammation in animal models, tissue is removed, Swiss-rolled and embedded in paraffin according to standard methods. The sections are stained with hematoxylin and eosin. The degree of colonic inflammation is graded semiquantitatively from 0 to 4 in a blinded fashion by a single pathologist using our usual standardized technique: 0=no inflammation; 1=low level inflammation;

2=intermediate level inflammation; 3=high level inflammation with wall thickening; and 4=transmural infiltration, and loss of goblet cells with wall thickening.

To count mast cells, intestinal tissue samples from individual mice are prepared by the Swiss-roll technique, fixed in Carnoy's fixative, paraffin embedded and processed for staining with Alcian Blue and safranin. Fifty adjacent fields of a given section are scanned for mucosal mast cells in the lamina propria and muscle layers. Mast cells are identified by their distinctive intracellular granular staining with Alcian Blue. All samples are evaluated blindly.

Disease activity in humans is monitored using various clinical, laboratory and histological criteria. There are several well established IBD disease activity indices that monitor clinical parameters like frequency of diarrhea and abdominal pain. One particularly useful index for the assessment of Crohn's disease is the Crohn's Disease Activity Index, or CDAI (Best et al., 1976, *Gastroenterology* 70: 439). The CDAI incorporates 8 variables related to the disease activity and has been used in most recent studies of therapeutic agents in Crohn's disease. It includes the number of liquid or very soft stools, the severity of abdominal pain or cramping, general well-being, the presence of extraintestinal manifestations of the disease, presence or absence of an abdominal mass, use of antidiarrheal drugs, hematocrit, and body weight. The composite score ranges from 0 to about 600. Scores below 150 indicate remission and scores above 450 indicate severe illness.

A tested, accepted and disease specific quality of life questionnaire also may be administered prior to and after treatment to assess therapeutic progress. The Irvine Inflammatory Bowel Disease Questionnaire is a 32-item questionnaire. It evaluates quality of life with respect to bowel function (e.g. loose stools and abdominal pain), systemic symptoms (fatigue and altered sleep pattern), social function (work attendance and the need to cancel social events) and emotional status (angry, depressed, or irritable). The score ranges from 32 to 224, with higher scores indicating a better quality of life. Patients in remission usually score between 170 and 190.

Also, helpful are endoscopic, x-ray and histological assessment of intestinal disease activity. C-reactive protein levels and blood cell sedimentation rate may also be monitored as systemic indicators of inflammation.

2. Rheumatoid Arthritis

Evaluation of Inflammation:

For mice with collagen-induced arthritis, mice are examined every other day and their paws scored as follows: 0, normal; 1, Erythema and mild swelling confined to the ankle joint or toes; 2, Erythema and mild swelling extending from the ankle to the midfoot; 3, Erythema and severe swelling extending from the ankle to the metatarsal joints; and 4, Ankylosing deformation with joint swelling. These four parameters can be correlated with the histological changes in the arthritic joints. Treatment success results in a decrease in the arthritis score with improvement in the histology.

For pristane-induced arthritis, joints may be measured with a micrometer to detect swelling. In humans, RA is scored by measuring joint swelling, erythema, limitation of motion and pain. Additionally, synovial fluid may be analyzed for cytokine and inflammatory protein concentrations, and for leukocyte composition and function, according to methods known in the art. Synovial biopsies provide tissue for histological analysis according to methods known in the art.

3. Lupus

Evaluation of Inflammation:

The normal development and function of the immune system critically depends on the removal of unwanted cells by a process called apoptosis. Cell-to-cell interactions through specific cell surface molecules and their receptors frequently trigger the process. One such system is called FAS and FAS ligand. Mice deficient in either FAS (LPR−/−) or FAS ligand (GLD−/−) develop an autoimmune disease like lupus.

Colonies of LPR or GLD mice are maintained in microisolator housing units under specific pathogen-free conditions. These mice can develop autoimmunity spontaneously, but more predictably after artificial induction. To induce disease, 8-wk-old mice are injected with an agent like pristane. Within two months, the mice have autoimmune disease. Many clinical, histological and immunological criteria useful for judging disease induction and amelioration in both mice and humans are well known in the art.

4. Juvenile Insulin-dependent Diabetes Mellitus (Type 1)

Evaluation of Inflammation:

The NOD mouse develops type 1 diabetes mellitus similar to humans due to autoimmune destruction of the pancreatic $\beta$ cells. Clinical, biochemical, immunological and histological examination according to methods known in the art allow assessment of disease induction and amelioration in mice.

5. Sarcoidosis

Evaluation of Inflammation:

In the bead embolization model of pulmonary inflammation, antigens (i.e. Th1 or Th2) are coupled to Sepharose beads, which are embolized to the lungs of mice via injection into their tail veins. The animals usually are pre-sensitized to the coupled antigen. The immune system of the host mounts a vigorous immune response to the offending bead. These focal inflammatory responses, which can last for several weeks, can be examined histologically for size. Also, they can be isolated from tissue and studied for cell composition and cytokine production. Moreover, hilar lymph nodes and spleens are readily available for experimentation.

Sarcoidosis, a disease of humans, usually involves the lung. Determination of sarcoidosis and the extent of the disease may be made according to methods known in the art. Pulmonary function tests can assess lung compliance and function. Also, bronchiolar lavage obtains inflammatory cells that have infiltrated into the bronchial tree during the inflammatory process. These cells can be studied for composition and function. Pulmonary infiltrates and hilar lymphadenopathy are characteristic of sarcoidosis. Thus, periodic chest x-ray or CT scans can help assess disease activity. Serologic tests, such as measurement of angiotensin converting enzyme activity according to methods known in the art, can be used to gauge disease extent and activity.

6. Multiple Sclerosis

Evaluation of Inflammation:

Experimental autoimmune encephalomyelitis is induced in susceptible mice by repeated injection of appropriate sensitizing myelin antigens. Mice are assessed clinically according to the following criteria: 0, no disease; 1, tail atony; 2, hind-limb weakness; 3, hind-limb paralysis; 4, hind-limb paralysis and fore-limb paralysis or weakness; 5, moribund. For histological analysis, the spinal cords and brains are removed and fixed in formalin. The paraffin-embedded sections are stained and examined under light microscopy. Dispersed splenocytes and cells from other regions can be studied in-vitro as outlined above. These parameters can help measure disease amelioration or improvement.

In humans, MS disease activity is gauged by monitoring progression and remittence of neurological signs and symptoms. The most widely used outcomes measurement is called The Expanded Disability Status Scale. Cerebral spinal fluid protein composition and cell content analyzed according to methods known in the art also may be used to monitor disease activity. Moreover, serial MRI studies show new gadblinium-enhanced brain lesions.

Animal Models Useful According to the Invention

The following Table I illustrates the disease conditions that can be prevented or treated by the helminthic parasites in accordance with the present invention.

TABLE 1

| TREATABLE DISEASES | SOME ANIMAL MODELS |
| --- | --- |
| 1. Inflammatory Bowel Diseases | TNBS colitis (Neurath et al., 1995, J. of Exp. Med. 182:1281)<br>IL-2 mutant mice (Ludviksson et al., 1997, J. of Immunol. 158:104)<br>IL-10 mutant mice (Berg et al., 1996, J. of Clin. Investigation 98:1010)<br>TCR transgenic mice (Mombaerts et al., 1993, Cell 75:274)<br>CD45+ T cells transferred into SCID mice (Powrie et al., 1994, Immunity 1:553) |
| 2. Rheumatoid Arthritis | Murine pristane-induced arthritis (Stasluk et al., 1997, Immunol. 90:81)<br>Murine collagen-induced arthritis (Horsfall et al., 1997, J. of Immunol. 159:5687) |
| 3. Insulin-dependent Diabetes (type 1) | NOD mouse (Cameron et al., 1997, J. of Immunol. 159:4686) |
| 4. Lupus | (NZWX NZB) $F_1$ models (Santiago et al., 1997, J. of Exp. Med. 185:65)<br>GRD, LPR mouse (FAS mutation) (Bhandoola et al., 1994, Int. Rev. of Immunol. 11:231) |
| 5. Sarcoidosis | Murine Berylliosis (Pfeifer et al., 1994, Int. Archives of Allergy & Immunol. 104:332)<br>M. avium mouse (Chen et al., 1994, Science 265:1237) |
| 6. Multiple Sclerosis | Experimental allergic encephalomyelitis in mice |

Mechanism of Action

This invention involves the prevention and/or treatment of autoimmune diseases in individuals by the administration of helminthic parasites, and to the prevention or vaccination and/or treatment of an excessive immune response or aberrant immune response in an individual due to IBD, Crohn's disease (CD), ulcerative colitis (UC), rheumatoid arthritis (RA), insulin-dependent, juvenile diabetes mellitus (DM) (type 1), lupus erythematosus (LE), sarcoidosis and multiple sclerosis (MS) by administration of helminthic parasite to that individual.

Without being bound to any one mechanism of action, the following mechanism is proposed.

Inflammation is a complex process involving many cell types and the release of various immunoregulatory molecules called cytokines. The types of cytokines secreted determine the nature of the inflammatory response. Immune responses usually present as either Th1 and Th2. Th1-type inflammations produce large amounts of IFN-γ and TNFα, which stimulate a strong cellular immune reaction to invading pathogens like bacteria, viruses and protozoa. A Th2-type response contains IL-4, IL-5, IgE, IgG1, mast cells and eosinophils. This type of inflammation is seen commonly in allergic reactions. Strong Th1 and Th2 responses are mutually exclusive. IFN-γ prevents expression of IL-4, and IL-4 impedes IFN-γ production, which are the two cytokines centrally important for the Th1 and Th2 patterns of inflammation. Also there are other cytokines like IL-10 and TGF-β that inhibit IFN-γ synthesis.

The immune response to helminthic parasites promotes Th2 responses to unrelated antigens. Infestation with helminthic parasites, which all induce Th2-type inflammation, can modulate the Th1 immune response to unrelated concomitant parasitic, bacterial and viral infections (Kullberg et al., 1992, *J. Immunol.* 148:3264). Patients infected with *S. mansoni* mount more of a Th2-like response to tetanus toxoid immunization than the usual Th1 or Th0 (Sabin et al., 1996, *J. Infec. Dis.* 173: 269). Ethiopian immigrants with a high prevalence of helminthic infections have eosinophilia and a propensity to respond to PHA with Th2, rather than Th1 cytokines (Bentwich et al., 1996, Clin. Exp. Immunol. 103: 239).

Animal experimentation supports this contention. Mice infected with *Mycobacterium avium* develop chronic Th1-type granulomatous inflammation in the lungs and liver. Splenocytes and granuloma cells from these infected animals normally produce IgG2a and IFN-γ, and no IL-4 or IL-5. However, mice infected with *S. mansoni* after the establishment of *Mycobacterium avium* infection form mycobacterial granulomas containing eosinophils. Also, splenocytes and granuloma cells from co-infected mice secrete more IgG1 and much less IgG2a. The cytokines released from these cells both constitutively or after mycobacterial antigen stimulation include IL-4 and IL-5, and much less than normal quantities of IFN-γ.

There are other examples. Infection of mice with *S. mansoni* delays clearance of vaccinia virus and alters responsiveness to sperm whale myoglobin. Mice also develop a Th2 response when infected with the microfilariae, *Brugia malayi*, or immunized with a soluble filarial extract from this parasite. The ongoing Th2 response to this helminth antigen modulates the Th1 response to mycobacterial antigen. Moreover, *Nippostrongylus brasiliensis*, a murine intestinal nematode, stimulates Th2 activity. *Nippostrongylus* delays kidney graft rejection in rats.

EXAMPLES

The invention is illustrated by the following nonlimiting examples wherein the following materials and methods are employed. The entire disclosure of each of the literature references cited hereinafter are incorporated by reference herein.

Example 1

General Methods

Animals: Colonies of 129/SV IL-10–/– mutant mice, and appropriate control animals are maintained are housed in facilities maintained as a specific pathogen-free environment according to standard methods.

Parasite Maintenance, Animal Infection, Production of Schistosome Eggs: The maintenance of *T. muris* and the method used for infection are as described by Else and Wakelin, 1990, *Parasitology*, vol. 100, part 3: 479.

Schistosome eggs were harvested from the livers of schistosome-infected hamsters and stored as described by Elliott, 1996, *Methods: A Companion to Methods in Enzymology*, 9:255. Five infected hamsters yield about $2 \times 10^6$ eggs.

Preparation of *T. suis* Eggs: The following process was used in the preparation and harvesting of *T. suis* eggs. Adult *T. suis* worms were isolated from the colon of pigs 7-8 wks after exposure to an experimental inoculation of *T suis* eggs. Embryonated eggs were obtained by culturing adult worms in vitro, and then the excreted eggs, separated from the culture medium by centrifugation, were placed into 0.2% potassium dichromate solution at 22° C. for 5-6 wks with bubbling to obtain infective first-stage larvae. Eggs were washed twice in sterile water by centrifugation at 1200×g for 10 min, counted, and re-suspended in the desired amount of saline based on a calculated dose of 2,500. These eggs were stored for use in the subjects. The ova are stable for at least one year in the refrigerator. To assure infectivity, we monitored patients for the appearance of ova in the stool after colonization. The number of ova in the stool is proportional to the intensity of the infestation. Also, from time to time, we infect pigs with our stored ova to assure continued infectivity.

Infection with *M. avium*: Mice were infected by injecting $10^6$ colony forming units (CFU) of *Mycobacterium avium* (ATCC 25291) intraperitoneally. On day 60 of infection, some mice also received 35 *S. mansoni* cercariae to induce dual infection.

Schistosome Infection and Isolation of Ova: Some experiments used mice (18-20 g) infected for 8-9 wks with *S. mansoni*. Mice were infected subcutaneously with 40 cercariae from the Puerto Rican strain.

Granuloma Isolation and Dispersal: Granulomas form in schistosome-infected mice because of natural egg deposition, which begins at the 6th wk of infection. *M. avium* also induces granulomas. We study liver granulomas isolated from infected mice as described (Elliott, 1996, supra). Granulomas were dispersed to produce single-cell suspensions. Isolated granulomas were agitated for 35 min at 37° C. in a shaker water bath in RPMI medium containing 5 mg/ml collagenase. The residual granulomas were sucked and expelled through a 1 ml syringe to induce further dissociation. The resulting cell suspension was filtered through gauze and washed three times. Cell viability was determined by Eosin-Y exclusion. This protocol resulted in a high yield of viable inflammatory cells that show preserved surface molecule expression.

Spleen and MLN Dispersal: Splenocytes and MLN were dispersed by teasing and washing the tissue through a stainless steel mesh. The contaminating RBC were lysed with H20, and the cells were washed ×3 in RPMI before use.

Induction of TNBS Colitis: Colitis was induced by rectal instillation of trinitrobenzesulfonic acid (TNBS) as described by Neurath et al., 1995, J. Exp. Med., 182:1281. Briefly, control or parasite-exposed BALB/c mice were fasted for 30 hrs then anesthetized with methoxyflurane. A 1.2 mm catheter was advanced 4 cm into the colon and 0.1 ml of TNBS solution (5 mg/ml TNBS (Sigma) in 50% ethanol) was instilled. The animal was held by the tail for 3 minutes to insure uniform contact with colonic mucosa.

Evaluation of Mucosal Inflammation: To grade intestinal inflammation, tissue was removed at the indicated time points, Swiss-rolled and embedded in paraffin according to standard methods. The sections were stained with hematoxylin and eosin. The degree of colonic inflammation was graded semiquantitatively from 0 to 4 in a blinded fashion by a single pathologist using our usual standardize technique (19). O=no inflammation, 1=low level inflammation, 2=intermediate level, 3=high level inflammation with wall thickening, 4=transmural infiltration, loss of goblet cells, wall thickening.

ELISAs for Murine Cytokines: ELISAs were performed as described in section VI, above.

Example 2

Th2 Response to *S. mansoni* Down-modulates an Ongoing Th1 Response to an Unrelated Bacterial Th1-inducing Antigen It is well established that Th cell immune responses can polarize into Th1 or Th2 patterns. This polarization occurs because IFNγ from Th1 cells inhibits proliferation of Th2 cells, while IL-4 and IL-10 from Th2 cells inhibits development of Th I cells. The following experiments demonstrated that schistosomiasis alters the murine Th1 response to an established mycobacterial infection.

Figure 1B:
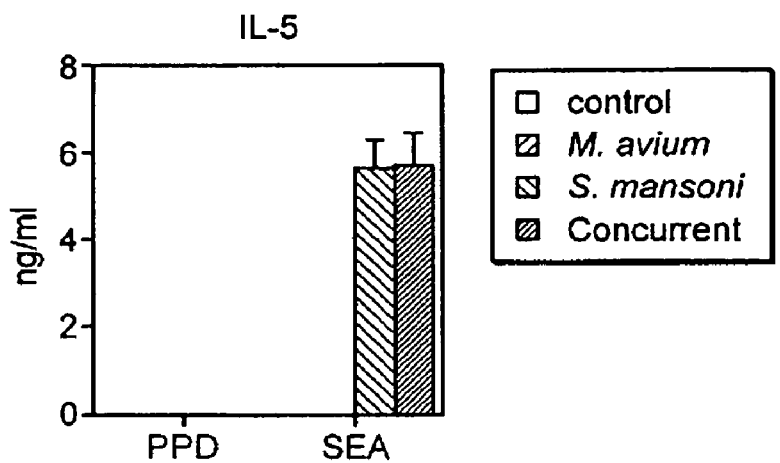
Figure 1C:
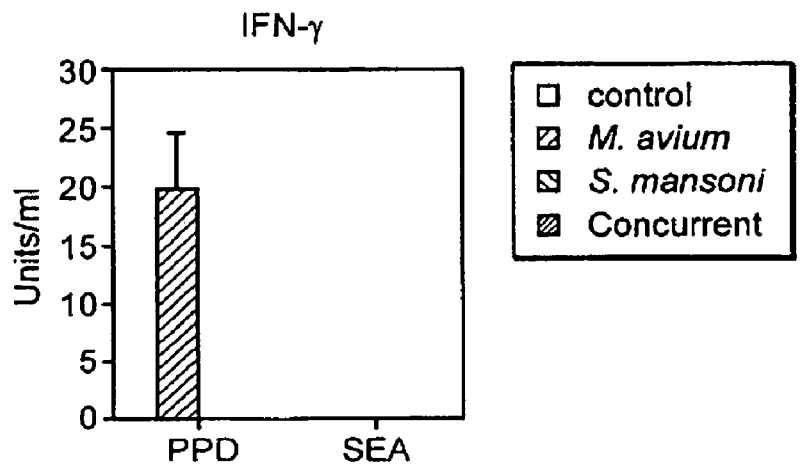
Figure 2A:
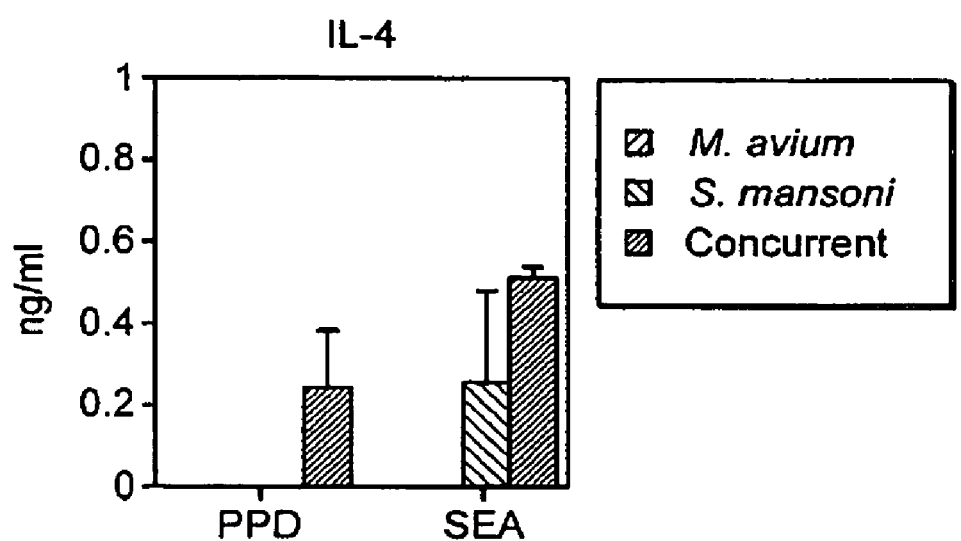
FIG. 2. The figure describes the concentrations of IFNγ and IL-4 in granuloma cell supernatants of mice infected with *M. avium, S. mansoni* or both organisms. Granuloma cells ($4 \times 10^5$/well) in 200 μl of medium were cultured in vitro at 37° C. for 48 h in the presence or absence of the optimal concentration of PPD or SEA. Cytokines were quantified by ELISA.
Figure 2B:
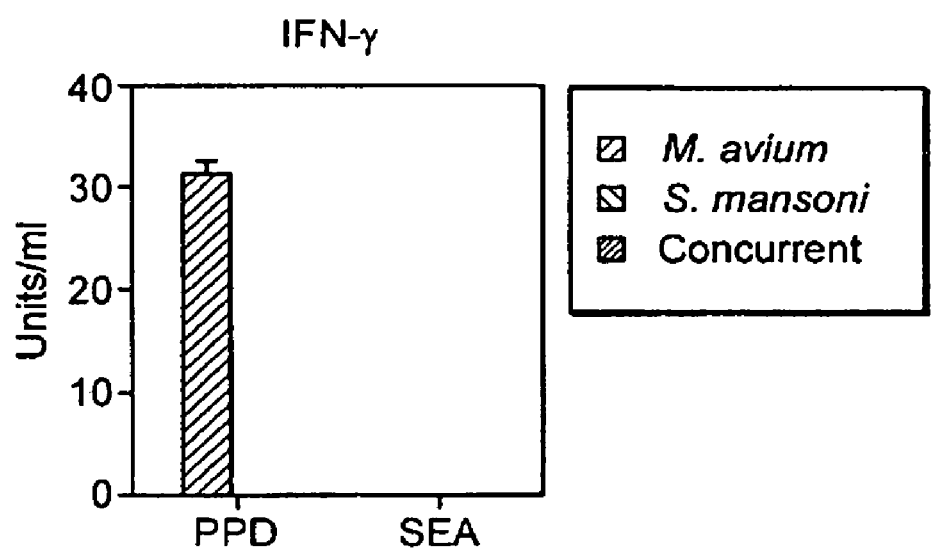
Figure 3A:
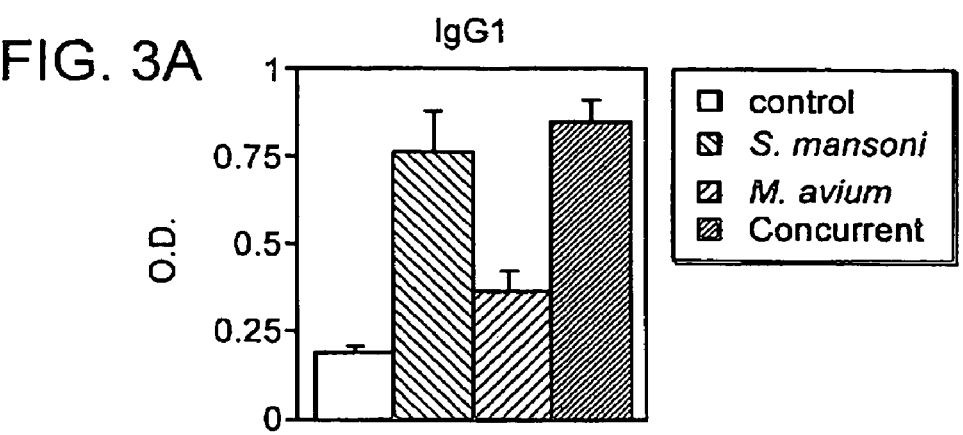
FIG. 3. The figure describes the serum IgG1, IgE and IgG2a levels measured in mice infected with *M. avium, S. mansoni* or both (concurrent). Immunoglobulin concentration was determined by ELISA.
Figure 3B:
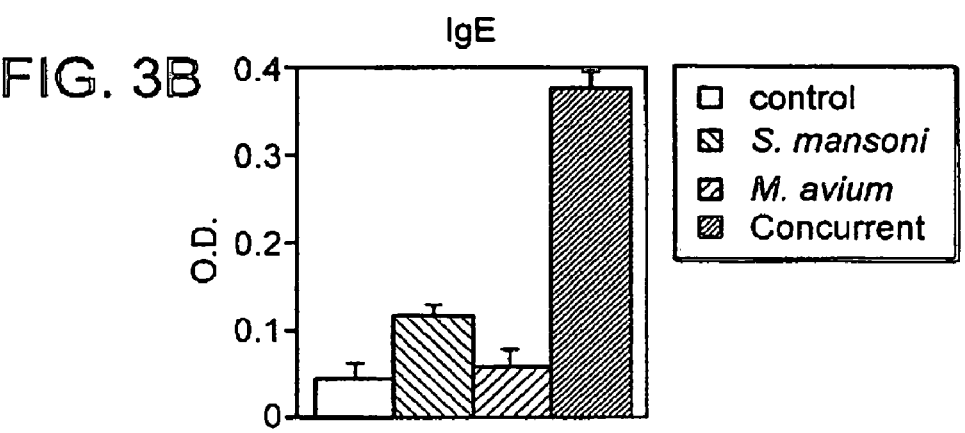
Figure 3C:
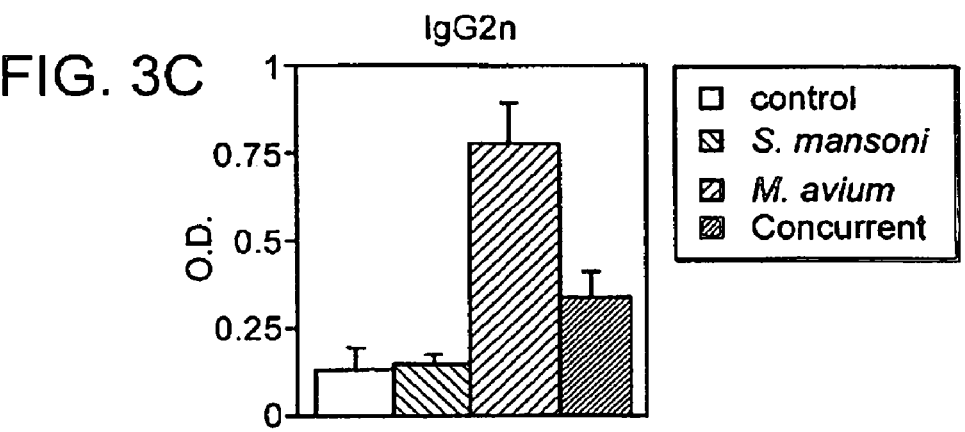

Mice were co-infected with *M. avium* and *S. mansoni* to evaluate the host response to these distinctly different Th1 and Th2 inflammatory stimuli. BALB/cAnN mice develop chronic *M. avium* infection when injected with this organism ($10^6$ CFU). Sixty days after establishment of the mycobacterial infection, the mice were infected with *S. mansoni* (40 cercariae). The mice were killed sixty days later. Control groups included mice receiving either *M. avium* only for 120 days or *S. mansoni* only for 60 days. Dispersed splenocytes or isolated granuloma cells from these animals were cultured in vitro ($4 \times 10^5$ cells/well) for 48 h in the presence or absence of schistosome egg antigen (SEA, a strong Th2 antigen) or mycobacterial antigens purified protein derivative (PPD, a strong Th1-inducing antigen) used at optimal concentration. After the incubation, supernatants were assayed for cytokine or immunoglobulin production using ELISAS. The data in FIGS. 1-3 are mean values+/−SD of three separate experiments. Splenocytes from mice infected only with *M. avium* secreted large amounts of IFNγ following stimulation with PPD (Th1 antigen). Spleen cells from uninfected control mice produced none. Most importantly, no IFNγ was detected in spleen cell cultures from concurrently infected mice (*M. avium* alone vs. concurrent infection, P<0.001, FIG. 1).

Soluble schistosome egg antigen (SEA, Th2 antigen) stimulated only IL-4 and IL-5 release from splenocytes of *S. mansoni*-infected animals. Mice singularly infected with *M. avium* produced no IL-4 or IL-5 in response to PPD or SEA. However, splenocytes from co-infected animals secreted some IL-4 following PPD stimulation (FIG. 1).

Granulomas were isolated from the livers of mice infected with *M. avium* or *S. mansoni*, or from animals that had concurrent infection. Concurrently infected animals develop liver granulomas that contain both schistosome eggs and mycobacteria readily evident on histological examination. Dispersed granuloma cells from these animals were cultured in vitro for 48 h in the presence or absence of SEA or PPD used at optimal concentration. Granuloma cells from mice only infected with *M. avium* secreted large amounts of IFNγ following stimulation with PPD. No IFNγ was detected in granuloma cell cultures from concurrently infected mice (*M. avium* alone vs other, P<0.001) (FIG. 2). SEA stimulated IL-4 release from granuloma cells of *S. mansoni*-infected animals. SEA did not promote IFNγ secretion under any circumstance. Mice singularly infected with *M. avium* produced no IL-4 in response to PPD. However, granuloma cells from co-infected animals secreted some IL-4 following PPD stimulation (FIG. 2).

Th1 responses promote IgG2a production, whereas Th2 reactions enhance IgG1 and IgE. FIG. 3 shows that mice infected with *M. avium* have high serum IgG2a levels. Yet, co-infected animals have normal serum IgG2a concentrations, but increased IgG1 and IgE levels. These data taken together show that a Th2 response to a helminthic infection can down-modulate the ongoing host response to even a strong Th1-inducing organism like *M. avium*.

Example 3

Colonization with Intestinal Helminths or Exposure to Their Ova Attenuates Th1-type Gut Inflammation in Murine TNBS-induced Colitis Rectal instillation of TNBS in 50% ethanol induces a colitis in mice that shares features with Crohn's disease. The colonic inflammation is characterized by infiltrating CD4+ T cells with elevated IFNγ MRNA expression. Lamina propria T cells from TNBS treated mice secrete 50 fold more IFNγ and 5 fold less IL-4 than T cells from controls (Neurath et al., 1995, supra). Lamina propria mononuclear cells secrete 30 fold more TNFα than cells from control mice (Neurath et al., 1997, *Eur. J. Immunol.*, 27: 1743). Importantly, TNBS colitis can be prevented or improved by treatment with anti-IL-12 (Neurath et al., 1995, supra), anti-TNFα (Neurath et al., 1997, supra), or rIL-10 (Duchmann et al., 1996, *Eur. J. Immunol.*, 26: 934). TNBS-induced colitis also can be prevented by previous oral exposure to the hapten (Elson et al., 1996, *J. Immunol.*, 157: 2174) probably by increasing mucosal IL-4, IL-10 and TGFβ responses (Neurath et al., 1996, *J. Exp. Med.*, 183: 2605).

We established this TNBS colitis model using BALB/c mice in our laboratory. Rectal administration of TNBS (0.1 ml of 5 mg/ml stock) in 50% ethanol reproducibly produced colitis in these animals. For each of the TNBS experiments discussed below, parasite-exposed and control animals were administered the same preparation of TNBS on the same day by the same operator who was blinded to the treatment group.

A. Schistosomiasis Inhibits IFNγ Release from MLN and Spleen Cells of TNBS Treated Mice.

As described above, schistosomiasis inhibits the murine Th1 response to an established mycobacterial infection. We extended these observations to determine if schistosome infection alters the Th1 response in TNBS treated mice. Mice were infected with 35 *S. mansoni* cercariae by sc. injection. Worms mature and begin to lay eggs about 6 weeks after initiation of infection. Two weeks later (at 8 wks of infection), mice were treated with TNBS. The capacity of MLN and spleen cells to make IFNγ in response to T cell stimulation (anti-CD3) was examined several days later. As shown in Table 1, natural schistosome infection strongly inhibits IFNγ release from mesenteric lymph node (MLN) and spleen cells of TNBS-treated mice.

TABLE 1

Schistosomiasis Inhibits IFNγ Production from MLN and Splenic T Cells of TNBS-Treated Mice

| | α-CD3 stimulated IFNγ (ng/ml) | |
|---|---|---|
| Group | MLN cells | Spleen cells |
| Uninfected mice given TNBS | 3.2 ± 0.7 | 44.1 ± 2.3 |
| Schistosome-infected mice given TNBS | 1.9 ± 0.3[a] | 4.2 ± 0.4[b] |

Mean IFNγ (ng/ml) ± SE of triplicate determinations measured by ELISA.
[a]$p < 0.1$
[b]$p < 0.05$
Cultures contained $10^6$ dispersed MLN or Spleen cells/well incubated in 200 μl medium for 48 hrs at 37° C. in the presence of anti-CD3 (1 μg/ml) (2C11). Results are representative of two experiments.

B. Exposure to Schistosome Ova Inhibits IFNγ Release from MLN and Spleen Cells of TNBS Treated Mice.

In schistosomiasis, it is exposure to the parasite ova rather than adult worms that induces a Th2 response. Schistosome infection does not induce strong Th2 responses until the worms mature and begin to lay eggs (Grzych et al., 1991, *J. Immunol.*, 146: 1322). Mice exposed to intact schistosome eggs in the absence of natural infection develop a strong Th2 response (Oswald et al., 1994, *J. Immumol.*, 153: 1707). These observations suggest that exposure to schistosome eggs in the absence of natural infection may induce Th2 and suppress Th1 responses.

We tested the hypothesis that pre-exposure to schistosome eggs would inhibit Th1 responses without requiring infection by adult worms. Mice were inoculated twice with $10^4$ schistosome eggs by intraperitoneal (ip) injection at 14 and 4 days prior to rectal challenge with TNBS. These times were chosen to model the continuous egg deposition that occurs in natural infection. Mice not exposed to parasite eggs but treated with TNBS served as controls. The eggs were previously frozen and were not viable at the time of injection. Once again, the capacity of MLN and spleen cells to make IFNγ in response to T cell stimulation (anti-CD3) was examined several days after TNBS instillation. Like natural schistosome infection (Table 1), ip. egg exposure inhibited IFNγ production from MLN and splenic T cells of TNBS-treated mice as shown in Table 2.

TABLE 2

Exposure to Schistosome Eggs Inhibits IFNγ Production from MLN and Splenic T Cells of TNBS-Treated Mice

| | α-CD3 stimulated IFNγ (ng/ml) | |
|---|---|---|
| Treatment | MLN cells | Spleen cells |
| TNBS alone | 4.65 ± 0.02 | 47.1 ± 3.0 |
| Eggs ip. and TNBS | 2.19 ± 0.11[a] | 21.8 ± 3.4[b] |

Mean IFNγ (ng/ml) ± SD of triplicate determinations measured by ELISA.
[a]$p < 0.5$.
Cultures contained $10^6$ dispersed MLN or spleen cells/well incubated in 200 μl medium for 48 hrs at 37° C. in the presence of anti-CD3 (1 μg/ml) (2C11). Results are representative of three separate experiments.

C. Exposure to Schistosome Ova Protects Mice from TNBS-induced Colitis.

Inhibiting development of the mucosal Th1 response can attenuate TNBS-induced colitis. Prior exposure to schistosome eggs inhibits Th1 cytokine secretion by MLN and splenic T cells. We next ascertained if ip injection of schistosome eggs would inhibit TNBS-induced colitis. Eggs were injected as above followed by TNBS treatment. Egg treatment dramatically reduced cumulative mortality in three separate experiments from 60% (16/27) in the control group to 22% (6/27) in egg-exposed mice. Intestinal inflammation was scored on a 4-point scale as detailed in General Methods, above. In the mice that survived, egg treatment attenuated intestinal inflammation from 3.1±0.5 (mean±SD) in the control group to 1.3±0.3 in the egg exposed mice (p<0.05, FIG. 4). Subsequent experiments showed that the largest difference between groups was evident at 3 days after TNBS treatment. Other experiments carried out to 14 days after TNBS instillation showed that egg exposure afforded prolonged protection. These data indicate that schistosome eggs protect mice from developing fatal colitis by inhibiting mucosal Th1 responses.

D. Intestinal Helminths Induce Host Th2 Responses.

Figure 4:
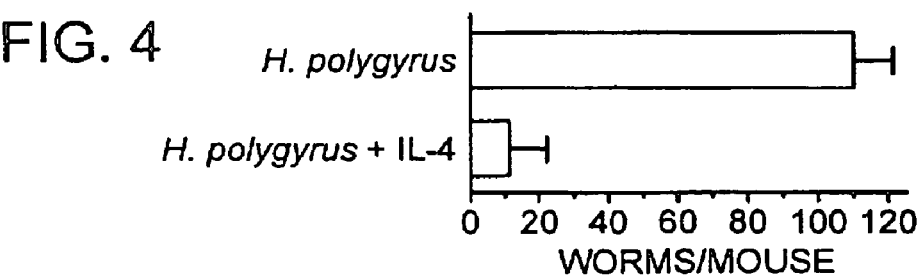
FIG. 4. The figure shows that IL-4 treatment can cure mice of a chronic *H. polygyrus* infection. Mice received three injections of an IL-4 complex starting 12 days before killing. Data are means+/−SE of multiple determinations.

It is probable that helminthic parasites other than *S. mansoni* can modulate host Th1 responses. Expression of protective immunity to intestinal nematodes is CD4 T cell-dependent. Mice expel worms or limit infection by mounting a Th2 response. Worm expulsion does not appear to exclusively depend on intestinal eosinophilia nor mucosal mastocytosis. IL-4 may have a critical role in worm expulsion, since treatment with blocking anti-IL-4 or anti-IL-4 receptor mAb promotes worm retention (Else et al., 1994, J. Exp. Med., 179: 347). Conversely, treatment with IL-4 promotes worm clearance (FIG. 4).

*T. muris* lives in the colon of the murine host. It is related to *Trichuris trichiura*, a parasite carried by nearly one billion people during their lives (Grencis et al., 1996, *Gastroenterology Clinics of North America*, 25: 579). Ingestion of eggs initiates infection. The eggs release larvae that penetrate the cecal epithelium. They then mature into adult worms. The parasite does not replicate within the host allowing us to control the intensity of infection (Bancroft et al., 1994, Eur. J. Immunol., 24: 3113).

We used *T. muris* to down-modulate intestinal Th1 responsiveness. *T. muris* infection is established by oral gavage with 250 embryonated eggs containing viable larvae. BALB/c mice can harbor *T. muris* and naturally expell the worms within 4 wks of infection. We treated *T. muris*- or sham-infected mice with rectal instillation of TNBS 4 wks after initiation of infection. Prior colonization with *T. muris* reduced cumulative mortality in two separate experiments from 58% (7/12) in the sham infected group to 21% (3/14) in the parasite exposed group. Furthermore, mice previously colonized with *T. muris* develop attenuated TNBS colitis (0.92±0.5, mean±SD) as compared to sham-infected mice (3.13±0.63, p<0.05). These data indicate that prior exposure to intestinal parasites (*T. muris*) protect mice from developing severe Th1-mediated colitis.

Example 4

IL-10 Gene Disruption does not Significantly Alter the Host/Parasite Interaction.

IL-10 is an important immunoregulatory cytokine that down modulates macrophage activation and accessory cell function (Moore et al., 1993, *Ann. Rev. Immunol.*, 11: 165). Mice rendered IL-10 deficient by targeted gene disruption (IL-10-/-) develop a chronic enterocolitis that is influenced by colonic flora (Kuhn et al., 1993, *Cell*, 75: 263). The intestinal inflammation is attenuated by treatment with anti-IFNγ antibody demonstrating that the colitis results from overly exuberant Th1 responses to colonic contents (Berg, et al., 1996, *J. Clin. Invest.*, 98: 1010). These mice serve as excellent models for spontaneous colitis similar to that of Crohn's disease. In this example we have used IL-10-/- mice on the 129 and C57Bl/6 backgrounds.

A. Disruption of the IL-10 Gene does not Alter Host Susceptibility to Parasite Colonization.

IL-10-/- mice spontaneously develop chronic intestinal inflammation. A potential concern was that this inflammation might prevent effective colonization with *T. muris*. We have found, however, that we routinely (>95%) obtain patent colonization with *T. muris* in IL-10-/- mice on both the 129 and C57Bl/6 backgrounds. To date, we have colonized more than 40 IL-10-/- mice with *T. muris*. IL-10 deficient mice also can harbor *S. mansoni* that mature to adult worms and lay eggs (Wynn et al., 1998, *J. Immunol.*, 160: 4473). We have confirmed these findings (see below).

B. IL-10-/- Mice can Mount Th2 Responses to Parasites.

Mice infected with the intestinal nematode *N. brasiliensis* develop Th2-type inflammation to the parasite with production of IL-4, IL-5 and IL-10. *N. brasiliensis* can colonize IL-10-/- mice and stimulate an appropriate intestinal Th2 response (Kuhn et al., 1993, supra). We infected IL-10-/- mice with *S. mansoni* to examine whether they mount a TH2 response. Table 3 shows that splenocytes from IL-10 gene-disrupted mice colonized for 8 wk with *S. mansoni* secrete large amounts of IL-4 upon stimulation with schistosome egg antigen (SEA) or anti-CD3. The granulomas that surround schistosome eggs in these mice contain the usual high percentage (45-50%) of eosinophils, and make IL-4 and IL-5. Thus, they show an effective Th2 response. These data indicate that exposure to helminthic parasites like *S. mansoni* will induce a strong Th2 response even in the absence of IL-10.

TABLE 3

Schistosomiasis Induces a Th2 Response in IL10 Deficient Mice

| | Spleen Cells from a Schistosome-infected Mice | | |
|---|---|---|---|
| Cytokine | Unstimulated | SEA-Stimulated | α-CD3 Stimulated |
| IL-4 (ng/ml) Wild Type | 0.07 ± 0.08 | 0.21 ± 0.02 | 3.94 ± 0.12 |
| IL-10-/- | 0.41 ± 0.10 | 2.56 ± 0.23 | 5.06 ± 0.33 |

Mean IL-4 (ng/ml) ± SD of triplicate determinations as measured by ELISA.
Cultures contained $10^6$ cells/well incubated for 48 hrs at 37° C. in 200 μl medium in the absence or presence of schistosome egg antigen (SEA 5 μg/ml) or anti-CD3 (1 μg/ml) (2C11). Results are representative of two separate experiments using a minimum of four wild type and KO mice in each experiment.

D. Helminthic Th2-conditioning Inhibits Natural Development of Mucosal Inflammation in IL-10-/- mice.

We showed that IL-10 deficient mice could harbor helminthic parasites and mount a strong Th2 response. Because IL-10-/- mice can develop Th2 responses and harbor intestinal parasites, they serve as excellent models to study the effect of parasite exposure on spontaneous or ongoing colitis. IL-10 is an important anti-inflammatory cytokine. It is possible that disruption of this essential immunoregulatory circuit will prevent mucosal Th2 conditioning by parasites. Present evidence indicates that infection with *T. muris* impedes the spontaneous colitis that develops in IL-10-/- mice. Animals (6-wk-old) received *T. muris* or sham infection and were killed 6 wks later. Colonic inflammation of *T. muris* or sham-infected IL-10−/− mice was scored on a 4-point scale as detailed in General Methods, above. Prior infection with *T. muris* attenuated intestinal inflammation from 3.0±0.3 (mean±SE) in the sham-infected group to 2.2±0.1 (p<0.05) in the parasite exposed IL-10−/− mice. These data demonstrate that prior exposure to helminthic parasites attenuates spontaneous colitis in IL-10 deficient mice.

Example 6

Intestinal Colonization with *Trichuris suis* Down-modulates Disease Activity in Patients with Crohn's Disease Our major hypothesis is that failure to obtain helminthic infections and experience mucosal Th2 conditioning during childhood predisposes to Crohn's disease and other autoimmune diseases which are the result of overly active Th1 reactions. An important corollary hypothesis is that colonization with intestinal parasites will down modulate established inflammation. We expect that this is possible because concurrent schistosomiasis impedes Th1 responses in an established *M. avium* infection (see above). We tested this hypothesis by colonizing patients with Crohn's disease with *Trichuris suis* and assessing improvement in disease activity.

*T. suis*, the porcine whipworm, is closely related to *T. trichiura*, a human intestinal helminth common in underdeveloped countries. The whipworm is a potential agent for therapy. The natural human parasite *Trichuris trichiura* is a very small organism that resides in the colon by attachment to the mucosa. Ordinary colonization usually produces no symptoms and causes no health problems for the host. This is the case in millions of colonized people throughout the world, but in a minority, heavy infestation produces diarrhea, bleeding and iron deficiency anemia. It is of interest that the parasite's life cycle is such that the host is not self-infected. The eggs would require a soil phase for maturation to become infective and then must be re-ingested to increase the parasitic load for an individual. Thus, *T. trichiura* infestation will not increase within the host unless eggs in the soil are ingested. The agent is readily and effectively treated with three days of mebendazole. The human whipworm could be used to colonize the host and be considered as an experimental agent to modify the immune process in Crohn's disease.

However, *Trichuris trichiura* poses a potential health problem for the host. Because the human is the only natural host, eggs for experimental use would have to be harvested from other humans, creating the potential for transmission of other human infectious diseases to the experimental subject. Therefore, we instead used a closely related animal parasite, the porcine whipworm (*Trichuris suis*), that has the potential to temporarily colonize a human host without causing symptoms, disease, a co-infectious disease or a public health hazard.

The porcine whipworm is closely related to the species infecting humans. The two organisms are of the same family and are morphologically similar, but they belong to a different species and can be distinguished morphologically, developmentally and clinically. The porcine whipworm ovum is slightly larger, has a different shaped spine, and the rate of development from an egg to an adult is slower than that of *Trichuris trichiura* (Beer, 1976, *Res. Vet. Sci.*, 20:47). Importantly, we can obtain infective parasite ova from SPF animals.

We produced a supply of infective *T. suis* eggs as described above. The eggs were tested to confirm absence of contamination with enteric pathogens (e.g. *Shigella, Salmonella, Campylobacter, Yersinia*, and enterotoxic *E. coli*) and viruses (e.g. CMV, HSV, VZV, adenovirus and enteroviruses).

Two patients with advanced, medication-resistant Crohn's disease were colonized with *T. suis*. They tolerated the parasite with little or no symptoms attributable to this organism. Table 4 shows that after achieving patent colonization, both participants had a drop in CDAI values, diarrhea, and inflammatory indices. This result indicates that helminths are useful for modulating abnormal immune responses, including, but not limited to Crohn's disease.

TABLE 4

Patients with Crohn's disease may benefit from colonization with *T. Suis*.

| Patient | Parameter | Baseline[a] | Week 2[b] | Week 4[b] |
|---------|-----------|-------------|-----------|-----------|
| 1 | CDAI[c] | 250.2 | 269.9 | 147.4 |
|   | Stools/week | 67 | 101 | 49 |
|   | ESR[d] | 17 | 11 | 4 |
|   | C-reactive protein | <0.5 | <0.5 | <0.5 |
| 2 | CDAI | 341.3 | 169.6 | 136.7 |
|   | Stools/week | 77 | 27 | 25 |
|   | ESR | 19 | 7 | ND |
|   | C-reactive protein | 0.9 | <0.5 | <0.5 |

[a]Stable values at entry into study.
[b]Values at 2 and 4 weeks after initiation of colonization with *T. suis*.
[c]Crohn's disease activity index.
[d]Erythrocyte sedimentation rate.
ND; not determined.

OTHER EMBODIMENTS

Other embodiments will be evident to those of skill in the art. It should be understood that the foregoing detailed description is provided for clarity only and is merely exemplary. The spirit and scope of the present invention are not limited to the above examples, but are encompassed by the following claims.

The invention claimed is:

1. A pharmaceutical composition suitable for oral administration comprising an isolated and purified *T. suis* helminthic parasite preparation free of human bacterial, mycobacterial and viral pathogens, and a pharmaceutically acceptable carrier.

2. The composition of claim 1, wherein the helminthic parasite preparation is prepared from helminths selected from the group consisting of parasite, parasite extract, parasite eggs, parasite egg extract, parasite larvae, parasite larvae extract, parasite cercariae, and parasite cercariae extracts.

* * * * *